(12) United States Patent
Ardehali

(10) Patent No.: US 12,257,397 B2
(45) Date of Patent: Mar. 25, 2025

(54) CATHETER FOR PORTABLE LUNG ASSIST DEVICE

(71) Applicant: THE REGENTS OF THE UNIVERSITY OF CALIFORNIA, Oakland, CA (US)

(72) Inventor: Abbas Ardehali, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 17/583,101

(22) Filed: Jan. 24, 2022

(65) Prior Publication Data

US 2022/0355065 A1 Nov. 10, 2022

Related U.S. Application Data

(63) Continuation of application No. 15/332,741, filed on Oct. 24, 2016, now abandoned, which is a continuation-in-part of application No. PCT/US2015/027334, filed on Apr. 23, 2015.

(60) Provisional application No. 62/322,293, filed on Apr. 14, 2016, provisional application No. 62/092,387, filed on Dec. 16, 2014, provisional application No. 62/050,507, filed on Sep. 15, 2014, provisional application No. 61/983,804, filed on Apr. 24, 2014.

(51) Int. Cl.
*A61M 25/00* (2006.01)
*A61M 1/36* (2006.01)
*A61M 60/113* (2021.01)
*A61M 60/38* (2021.01)

(52) U.S. Cl.
CPC ........ *A61M 25/003* (2013.01); *A61M 1/3659* (2014.02); *A61M 1/3666* (2013.01); *A61M 25/0041* (2013.01); *A61M 25/005* (2013.01); *A61M 60/113* (2021.01); *A61M 60/38* (2021.01); *A61M 2025/0002* (2013.01); *A61M 2025/0031* (2013.01); *A61M 2210/125* (2013.01)

(58) Field of Classification Search
CPC .............. A61M 25/003; A61M 25/005; A61M 2025/0002; A61M 2025/0031; A61M 2210/125
See application file for complete search history.

(56) References Cited

U.S. PATENT DOCUMENTS 4,985,014 A * 1/1991 Orejola ................ A61M 60/117
600/16
5,688,245 A * 11/1997 Runge ................ A61M 60/562
600/16

(Continued)

*Primary Examiner* — Eric D. Bertram
(74) *Attorney, Agent, or Firm* — Riverside Law LLP

(57) ABSTRACT

The present invention relates to a catheter that minimizes or eliminates the recirculation of oxygenated blood. The catheter of the present invention can be used to drain blood from multiple points in the patient, namely the superior vena cava, right atrium, and the right ventricle, while returning blood to the patient's pulmonary artery. Further, the catheter of the present invention is less likely to be moved or dislodged than catheters currently available in the art, thus making the catheter particularly useful for portable lung assist devices. The present invention also relates to methods for inserting the catheter into the patient and using the catheter with a lung assist device.

2 Claims, 11 Drawing Sheets

(56) References Cited

U.S. PATENT DOCUMENTS

| | | | | |
|---|---|---|---|---|
| 5,738,649 A * | 4/1998 | Macoviak | ............ | A61M 25/1011 |
| | | | | 604/509 |
| 6,059,760 A * | 5/2000 | Sandmore | ............ | A61M 25/007 |
| | | | | 604/534 |
| 6,395,026 B1 * | 5/2002 | Aboul-Hosn | ........ | A61M 60/165 |
| | | | | 623/3.13 |
| 6,532,964 B2 * | 3/2003 | Aboul-Hosn | ........ | A61M 60/165 |
| | | | | 600/16 |
| 7,494,477 B2 * | 2/2009 | Rakhorst | .............. | A61M 60/113 |
| | | | | 600/16 |
| 8,231,519 B2 * | 7/2012 | Reichenbach | ....... | A61M 60/178 |
| | | | | 604/4.01 |
| 8,764,819 B2 * | 7/2014 | Taub | .................... | A61M 1/3656 |
| | | | | 600/16 |
| 8,992,454 B2 * | 3/2015 | Anand | .............. | A61M 25/0071 |
| | | | | 604/4.01 |
| 9,168,352 B2 * | 10/2015 | Kelly | ................. | A61M 25/0029 |
| 2005/0279370 A1 * | 12/2005 | Aboul-Hosn | ........ | A61M 1/3653 |
| | | | | 604/9 |
| 2009/0005725 A1 * | 1/2009 | Shorey | .............. | A61M 25/0029 |
| | | | | 29/525.01 |
| 2011/0040241 A1 * | 2/2011 | Wang | .................. | A61M 1/3659 |
| | | | | 604/9 |
| 2013/0281761 A1 * | 10/2013 | Kapur | ................. | A61M 60/531 |
| | | | | 600/16 |
| 2018/0001012 A1 * | 1/2018 | Ardehali | ............... | A61M 1/267 |

* cited by examiner

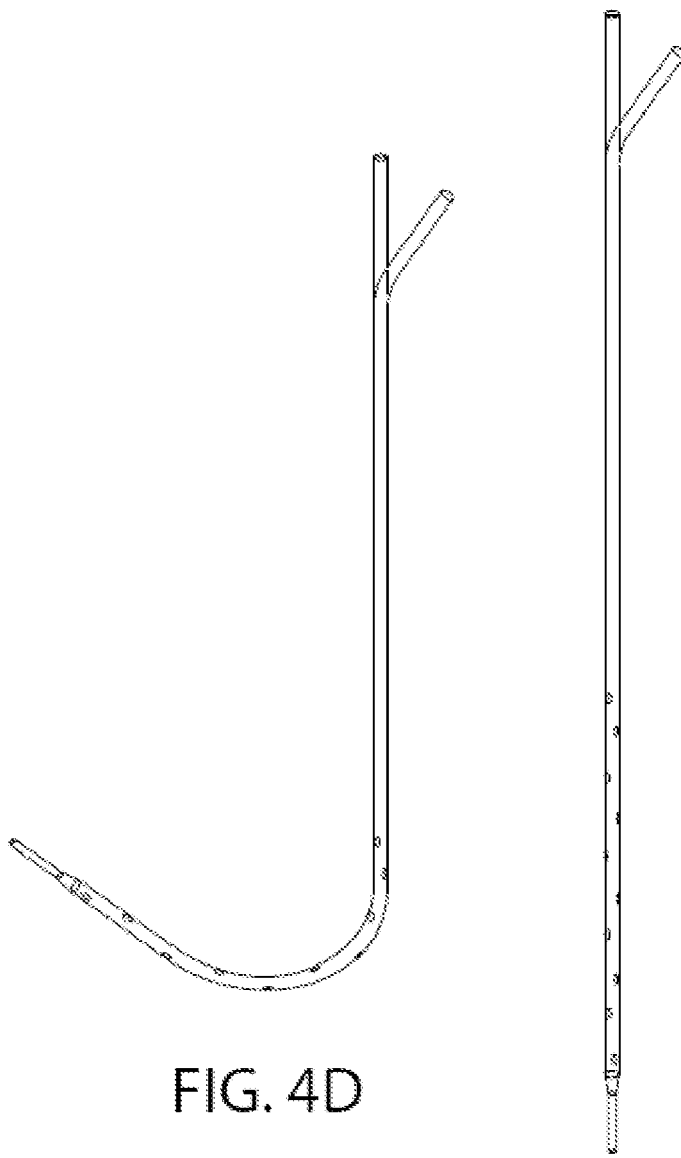
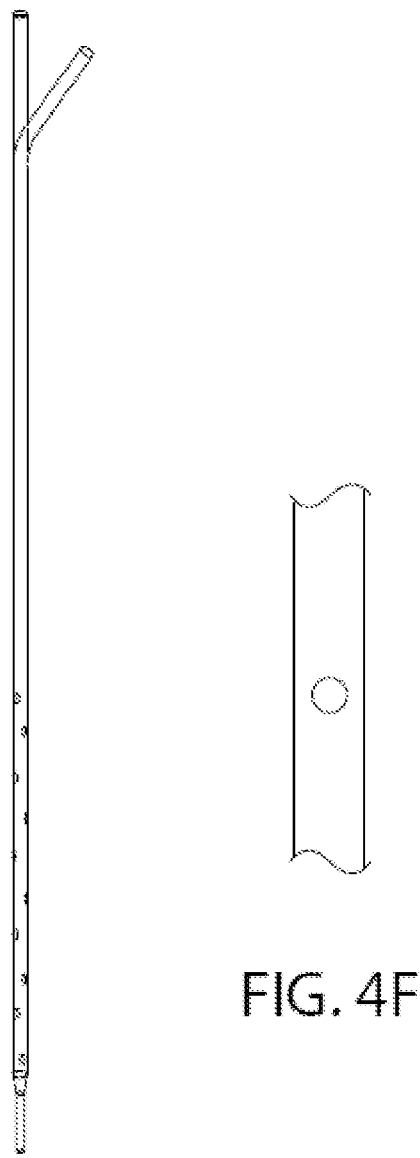
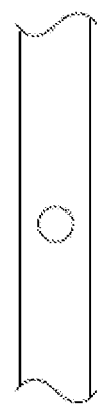
FIG. 4D
FIG. 4E
FIG. 4F

CATHETER FOR PORTABLE LUNG ASSIST DEVICE

CROSS-REFERENCE TO RELATED APPLICATIONS

This application a continuation of U.S. patent application Ser. No. 15/332,741, filed Oct. 24, 2016, which is a continuation-in-part of International Patent Application No. PCT/US15/27334, filed Apr. 23, 2015, which is entitled to priority under 35 U.S.C. § 119(e) to U.S. Provisional Patent Application No. 61/983,804, filed Apr. 24, 2014, No. 62/050,507, filed Sep. 15, 2014, and No. 62/092,387, filed Dec. 16, 2014, the contents of which are each incorporated by reference herein in their entirety. This application is also entitled to priority to U.S. Provisional Patent Application No. 62/322,293, filed Apr. 14, 2016, which is incorporated herein by reference in its entirety.

BACKGROUND OF THE INVENTION

Lung diseases are the third largest cause of mortality in the U.S., with more than 350,000 deaths annually attributed to lung disease. A wide range of disease processes culminate in end-stage lung disease, including adult respiratory distress syndrome (ARDS), chronic obstructive pulmonary disease (COPD), interstitial lung diseases, and cystic fibrosis. Patients with lung failure are usually treated with mechanical ventilation and sedation, with the hope that their native lung condition improves with therapy. In some patients that fail mechanical ventilation, veno-venous extracorporeal membrane oxygenation (ECMO) is used to support the patients' lungs as a bridge to recovery or lung transplantation.

Veno-venous ECMO usually requires dual cannulation sites: one for removal of unoxygenated blood and another for delivery of oxygenated blood, usually more centrally to minimize the risk of recirculation. The disadvantages of dual cannulation sites include patient immobility, risks of vascular injury, risks of infection, etc. Single site insertion using dual lumen catheters have been a major advance in the veno-venous ECMO space. For example, the Avalone Elite catheter (Maquet Holding) is a dual lumen catheter with the distinct advantage of single site (usually right internal jugular vein) cannulation. This catheter (FIG. 1A and FIG. 1B) removes the unoxygenated blood from the superior and inferior vena cava and directs oxygenated blood toward the tricuspid valve. Re-circulation of oxygenated blood is a limitation of the Avalone catheter. Additionally, changes in the position of the patient's neck can lead to changes in the direction of oxygenated blood flow and may exacerbate recirculation. Consequently, constant monitoring is required to detect and rectify recirculation of blood in patients using the Avalone catheter.

In another example, Shorey et al. (U.S. Patent App. Pub. No. 2009/0005725) and Kelly et al. (U.S. Patent App. Pub. No. 2013/0158338) both describe a single entry dual lumen cannulae with one lumen positioned in the right atrium for removal of unoxygenated blood and a second lumen positioned in the pulmonary artery for delivery of oxygenated blood. The drainage apertures of the catheters described in Shorey and Kelly are placed in the right atrium and away from the portion of the catheter in the right ventricle to minimize or prevent recirculation. Therefore, the design of Shorey and Kelly do not actively drain the right ventricle. A filled right ventricle that is not actively drained ejects unoxygenated blood into the pulmonary artery and decreases the efficiency of veno-venous ECMO.

The single-site entry dual lumen catheter may also be used in the setting of right ventricular failure (such as right ventricular infarct, right ventricular dysfunction after left ventricular assist device (LVAD) implantation, or right ventricular dysfunction after heart transplantation, etc.) to support the right ventricle. However, the current art does not actively and specifically drain the right ventricle. Active drainage of the right ventricle to allow remodeling and recovery is of critical importance in the setting of right ventricular failure, and may not be possible by the current art.

Thus, there is a continuing need in the art for veno-venous ECMO and right ventricular support that a) minimizes the recirculation of oxygenated blood, b) prevents or minimizes the need for re-positioning the catheter, or the risk of the catheter dislodging, due to patient movement, and c) effectively drains the right ventricle.

SUMMARY OF THE INVENTION

The present invention relates to a single-entry dual lumen catheter that has a first lumen that specifically drains the right ventricle in addition to the superior vena cava (SVC) and the right atrium. Blood is then returned via a second lumen into the pulmonary artery. This catheter minimizes or eliminates the re-circulation of blood, and ensures active decompression of the right ventricle.

In one aspect, the invention relates to a catheter comprising: a first tube having a proximal end, a distal end, and a length therebetween, and a lumen within the length of the first tube with at least one opening to the lumen near the distal end; a second tube having a proximal end, a distal end, and a length therebetween, and a lumen within the length of the second tube with at least one opening to the lumen at the distal end; and a preformed curvature near the distal end of the first tube and along the length of the second tube; wherein at least one of the openings of the first tube resides within the curvature, and wherein the distance of the at least one opening in the first tube residing in the curvature relative to the at least one opening in the distal end of the second tube is such that when the catheter is positioned in a subject's heart, the at least one opening in the first tube is positionable in the right ventricle while the at least one opening of the second tube is positionable in the pulmonary artery.

In one embodiment, the distal end of the second tube extends 50 to 150 mm past the most distal opening of the first tube. In one embodiment, at least one of the openings of the first tube is positionable in the superior vena cava when the catheter is positioned in the subject's heart. In one embodiment, at least one of the openings of the first tube is positionable in the right atrium when the catheter is positioned in the subject's heart. In one embodiment, the curvature of the catheter comprises a vertex or inflection point positioned 130 to 170 mm from the distal end of the second tube. In one embodiment, the distal end of the first tube is positioned at the vertex or inflection point of the curvature of the catheter.

In one embodiment, the catheter is sized for blood flow in the range of about 3 to 4 L per minute. In one embodiment, at least a portion of the first tube is reinforced with wire. In one embodiment, at least a portion of the second tube is reinforced with wire. In one embodiment, the catheter further comprises a means for measuring pressure in the patient's heart. In one embodiment, the means for measuring pressure comprises at least one pressure measuring lumen. In one embodiment, the curvature is between 110° and 120°.

In another aspect, the invention relates to a method for supporting a failing right ventricle in a subject, comprising: inserting a catheter into a subject, the catheter comprising a first tube having at least one opening connected to a lumen within, a second tube having at least one opening connected to a lumen within, and a preformed curvature, such that the catheter enters the subject's heart via the superior vena cava, passes through the right atrium, enters the right ventricle wherein the first tube terminates, and the curvature extends the second tube into the pulmonary artery; draining blood from the subject's right ventricle via the first tube; and pumping the blood to the subject's pulmonary artery via the second tube.

In one embodiment, the first and second tubes run substantially parallel to each other along at least a portion of the length of the catheter. In one embodiment, the first tube and second tube are coaxial along at least a portion of the length of the catheter. In one embodiment, blood is also drained from the subject's superior vena cava via the first tube. In one embodiment, blood is also drained from the subject's right atrium via the first tube. In one embodiment, the blood is oxygenated prior to pumping the blood to the subject's pulmonary artery via the second tube. In one embodiment, the blood is oxygenated using an extra-corporeal membrane oxygenation (ECMO) device. In one embodiment, the catheter is inserted into the subject using a guiding mechanism selected from the group consisting of: a guide wire, an X-ray guidance system, and an ultrasound guidance system.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 3A depicts an exemplary dual-lumen catheter with parallel tubes (not-to-scale). FIG. 3B depicts an exemplary dual-lumen catheter with coaxial tubes (not-to-scale).

FIG. 4A through FIG. 4F are a set of diagrams of an exemplary embodiment of a coaxial catheter of the present invention, including non-limiting examples of the dimensions of various portions of the catheter and the size and location of openings.

DETAILED DESCRIPTION

Figure 1B:
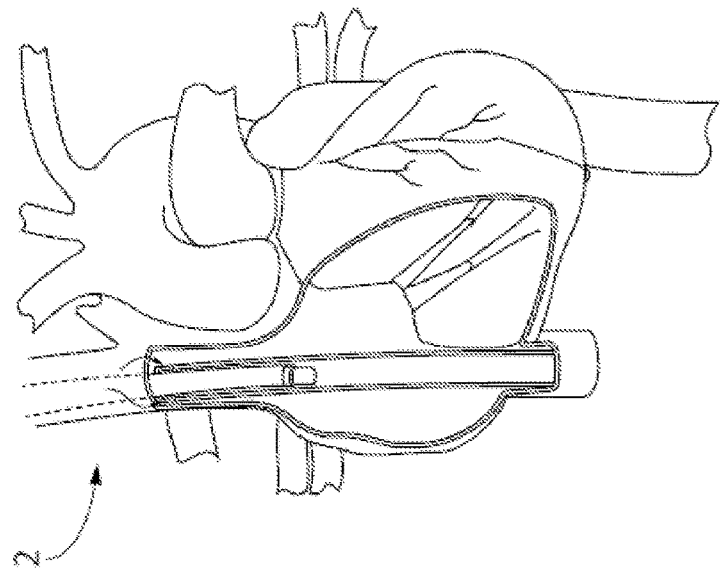
FIG. 1A through FIG. 1C are a set of illustrations showing a prior art catheter.

It is to be understood that the figures and descriptions of the present invention have been simplified to illustrate elements that are relevant for a clear understanding of the present invention, while eliminating, for the purpose of clarity, many other elements found in the field of catheters for use with ECMO and other lung assist devices. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate.

The terms "patient," "subject," "individual," and the like are used interchangeably herein, and refer to any animal amenable to the systems, devices, and methods described herein. Preferably, the patient, subject or individual is a mammal, and more preferably, a human.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Dual Lumen Catheters

The present invention relates in part to catheters having a plurality of lumens, and a method for using such catheters, that minimize or eliminate the recirculation of oxygenated blood and limit the circulation of unoxygenated blood. In addition, the catheters described herein can be used to drain blood from multiple points in the patient, namely the superior vena cava (SVC), right atrium, and the right ventricle. Further, these catheters are less likely to be moved or dislodged than catheters currently available in the art. These catheters are particularly useful in conjunction with an ECMO device and can significantly improve the efficiency of such devices. Additionally, these catheters provide efficient right ventricular support in the settings of right ventricular failure of various causes (e.g., right ventricular infarct, right ventricular failure in the setting of left ventricular assist device (LVAD) implantation, etc.). The catheters are able to support a failing right ventricle by removing blood from the right ventricle and right atrium and reinfusing it into the pulmonary artery, effectively and actively decompressing the right ventricle allowing recovery and remodeling of the right ventricle.

In one embodiment, the catheter is a dual lumen catheter, wherein a first lumen includes at least one opening that is used for draining blood from the superior vena cava, right atrium, and right ventricle. The drained blood can be sent to an ECMO device or other type of lung assist device for oxygenation. After the blood is circulated through the ECMO device and sufficiently oxygenated, the oxygenated blood is returned to the patient via the second lumen having at least one opening that is preferably positioned within the pulmonary artery.

Figure 1A:
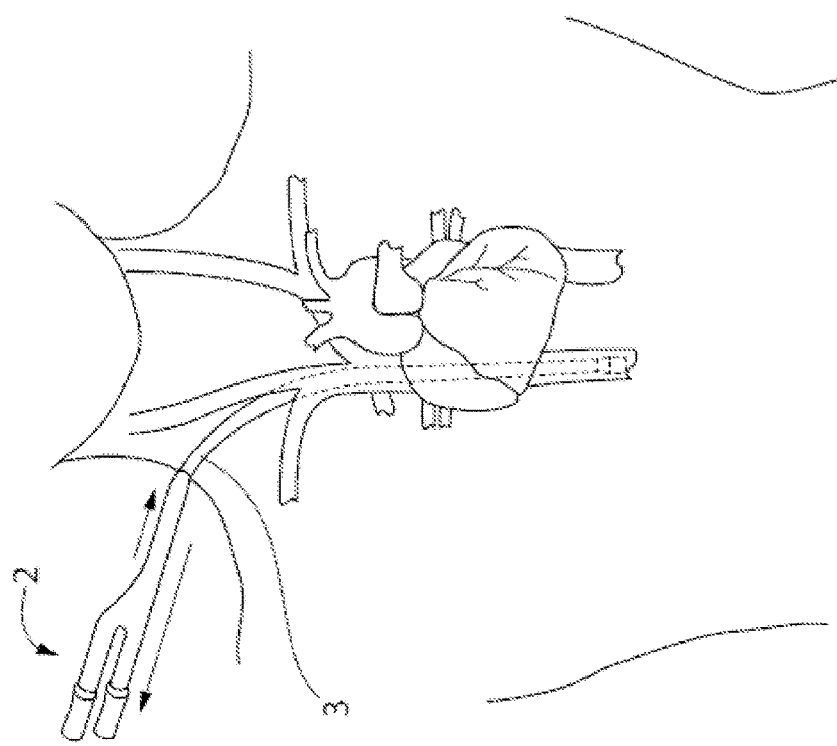
Figure 1C:
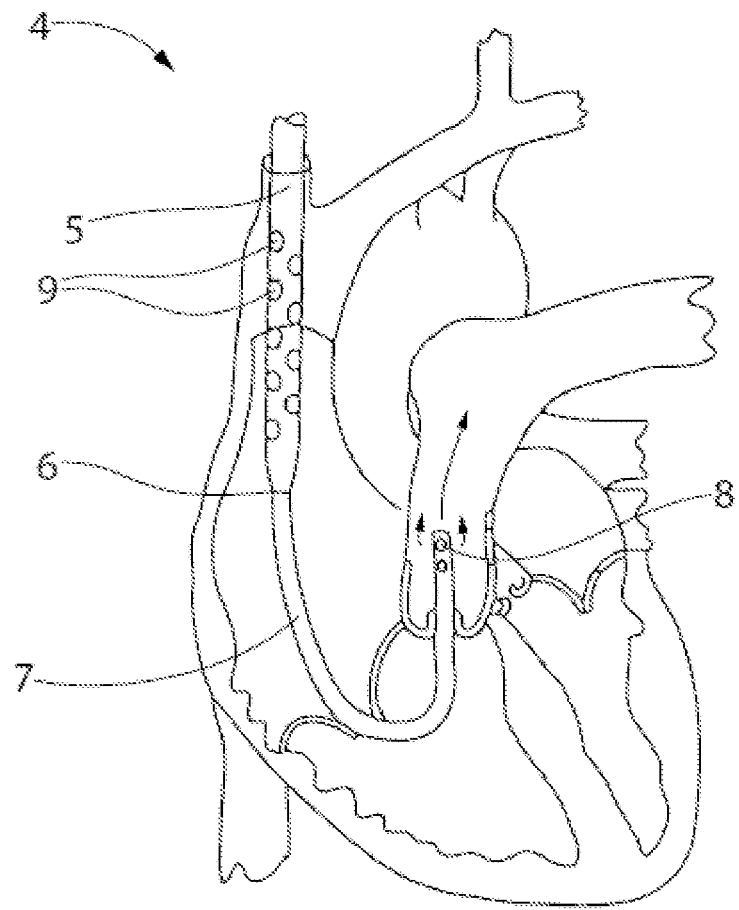

The most commonly used catheter in veno-venous ECMO devices is a dual lumen catheter that is configured to be placed in the right internal jugular vein. Referring now to FIG. 1A to FIG. 1C, currently known catheters are shown for purposes of comparison to the device of the present invention. This prior art catheter 2 comprises a single tube 3 having two lumens that can be inserted into the patient. Catheter 2 allows removal of venous (un-oxygenated) blood from the inferior vena cava (IVC) and superior vena cava via one lumen so that it can be sent to a lung assist device for oxygenation. Oxygenated blood is then returned to the patient via a second lumen into the right atrium, directed against the tricuspid valve, with the hope that the oxygenated blood will flow past the tricuspid valve and into the pulmonary circulation (see FIG. 1B). However, use of this catheter design is often associated with the recirculation of oxygenated blood within the patient, which reduces the efficiency of the lung assist device. Specifically, there is a significant amount of oxygenated blood that gets re-circulated, as some oxygenated blood will mix with the SVC and IVC blood and will return to the lung assist device for oxygenation, rather than flowing through the tricuspid valve. This re-circulation fraction is variable, depending on the position of the catheter, rotation of the catheter, and the patient volume status. Further, since the performance of this type of catheter is very much dependent on its position, any patient movement, e.g., flexion and extension of the neck, will move the catheter and result in changes in the position of the outflow hole against the tricuspid valve. It is not unusual that repeated trans-esophageal studies on the same patient will be required to re-position the catheter, as the patient awakens and invariably moves his or her neck. Accordingly, the efficiency of this catheter is very much dependent on its position, which can change significantly.

Conversely, the catheters of the present invention minimize or prevent recirculation of oxygenated blood by providing adequate spacing between the inflow and outflow openings, and by segregating the inflow and outflow openings within different areas of the patient's circulatory system. Specifically, the catheters of the present invention have one or more outflow openings located in the pulmonary artery, while the inflow openings are located within the right atrium, right ventricle, and/or superior vena cava. Thus, the outflow openings are separated by the inflow openings located in the right ventricle via the pulmonary valve in the pulmonary artery. The inflow openings located in the right atrium and superior vena cava are further separated from the outflow openings by the tricuspid valve. On the other hand, the outflow openings in prior art catheter 2 are not sufficiently segregated from the inflow openings to prevent significant recirculation of oxygenated blood. Further, prior art catheter 2 is not sufficiently stabilized in comparison to the catheters of the present invention because no parts of catheter 2 are positioned through either the tricuspid or pulmonary valves.

Referring now to FIG. 1C, another prior art catheter (from Shorey et al. (U.S. Patent App. Pub. No. 2009/0005725) and Kelly et al. (U.S. Patent App. Pub. No. 2013/0158338), described elsewhere herein) is shown for purposes of comparison to the devices of the present invention. Catheter 4 is a dual lumen catheter wherein the two lumens are coaxial. The tube 5 containing the outer lumen does not extend the full length of the catheter, but instead the outer wall of tube 5 is fused to the wall of the inner lumen at a point 6 within the right atrium. The tube 7 containing the inner lumen then is fed through the tricuspid valve and right ventricle and into the pulmonary artery, wherein oxygenated blood can be returned to the patient via openings 8. Tube 5, containing the outer lumen, has a number of openings 9 for draining un-oxygenated blood from the SVC and right atrium. However, tube 5 is not capable of draining blood from the right ventricle because tube 5 does not have any openings positioned within the right ventricle that are in communication with the outer lumen. Rather, catheter 4 merely accomplishes a reduction in blood flow to the right ventricle by virtue of draining blood upstream in the right atrium. Catheter 4 cannot effectively reduce blood volume in the right ventricle as regular pumping from the heart and valveless Thebesian veins will continuously pass blood into the right ventricle. The design of catheter 4 leads to several disadvantages, including circulation of unoxygenated blood and excessive loading of the right ventricle. As described elsewhere herein, patients receiving veno-venous ECMO treatment have struggling lungs that need support in oxygenating blood. Without sufficient drainage of unoxygenated blood from the right ventricle, the efficiency of veno-venous ECMO treatment is impeded due to unoxygenated blood from the right ventricle being pumped past the pulmonary valve into the pulmonary artery to mix with returned oxygenated blood. Furthermore, patients receiving this device for right ventricular failure are faced with a parallel problem. Without active draining of the right ventricle, the right ventricle is subjected to sustained distension, hindering recovery. Active decompression of the failing right ventricle is deemed critical in optimal recovery/remodeling of the right ventricle.

Accordingly, catheter 4 cannot drain blood from the right ventricle. Therefore, the catheters of the present invention have a significant advantage over catheter 4 because a) in veno-venous ECMO therapy, it actively decompresses the right ventricle and improves the efficiency of ECMO therapy, and b) in right ventricular failure, it actively decompresses the right ventricle and improves right ventricular remodeling and recovery.

Figure 2:
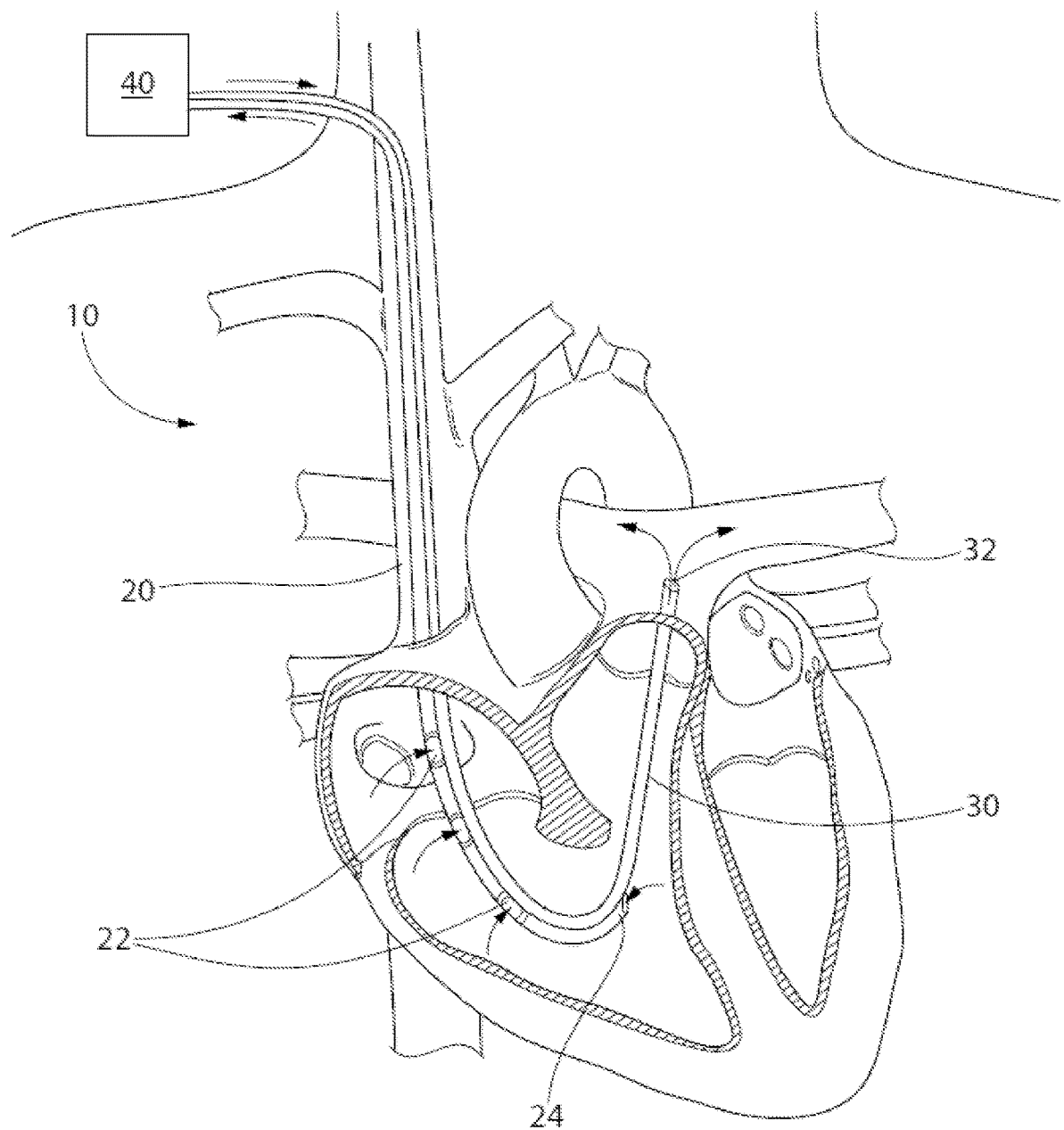
FIG. 2 is a diagram of an exemplary embodiment of a catheter positioned within a subject's heart.

Referring now to FIG. 2, an exemplary embodiment of a catheter 10 of the present invention is shown. Catheter 10 comprises a first tube 20, having a lumen for directing the inflow of blood from the patient to a lung assist device 40, and a second tube 30, having a lumen for directing the outflow of blood from lung assist device 40 back into the patient. As shown in FIG. 2, first tube 20 can be positioned so that it extends through the tricuspid valve and into the right ventricle. First tube 20 comprises one or more openings 22 in the wall of the tube for draining blood from the superior vena cava, right atrium, and/or right ventricle into the lumen of first tube 20. First tube 20 also comprises an opening 24 at or near its distal tip, which can be used to drain blood specifically from the right ventricle. Second tube 30 of catheter 10 is positioned so that it extends through the tricuspid valve and right ventricle, and through the pulmonary valve into the pulmonary artery, so that an opening 32 at or near the tip of second tube 30 can be used to send oxygenated blood directly into the pulmonary artery. In one embodiment, second tube 30 can also include one or more openings in the wall of the tube, particularly near the tip of the tube, instead of or in addition to opening 32. In another embodiment, opening 32 is preferably positioned such just past the pulmonary valve within the pulmonary trunk. Pushing the distal tip of a catheter past the pulmonary trunk is not ideal, as there is a risk that the catheter could puncture the pulmonary artery. In the event that a catheter tip pushed past the pulmonary trunk does not puncture the artery wall, there is still the potential for damage and hypoxia to the subject as an overextended catheter tip will necessarily be diverted to either the left or the right pulmonary artery, leading to an imbalance in the flow of oxygenated blood being directed down only the left pulmonary artery or only the right pulmonary artery. It should thus be appreciated that at least opening 24 relative to opening 32 must be of a specific distance apart to allow both drainage from the right ventricle while returning oxygenated blood flow at the beginning of the pulmonary artery just past the pulmonary valve in the pulmonary trunk.

Figure 3A:
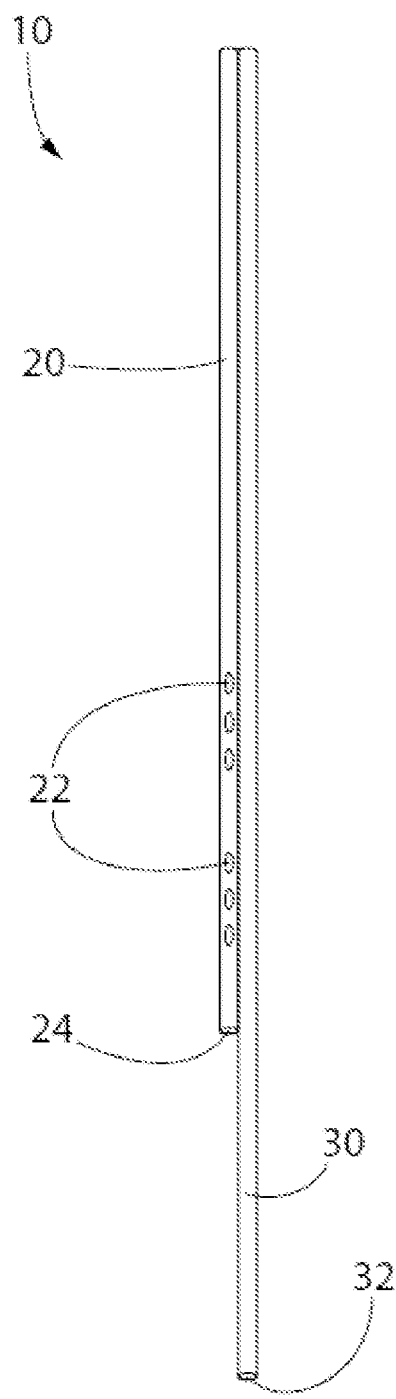
FIG. 3A and FIG. 3B are illustrations showing two exemplary embodiments of the device of the present invention.
Figure 3B:
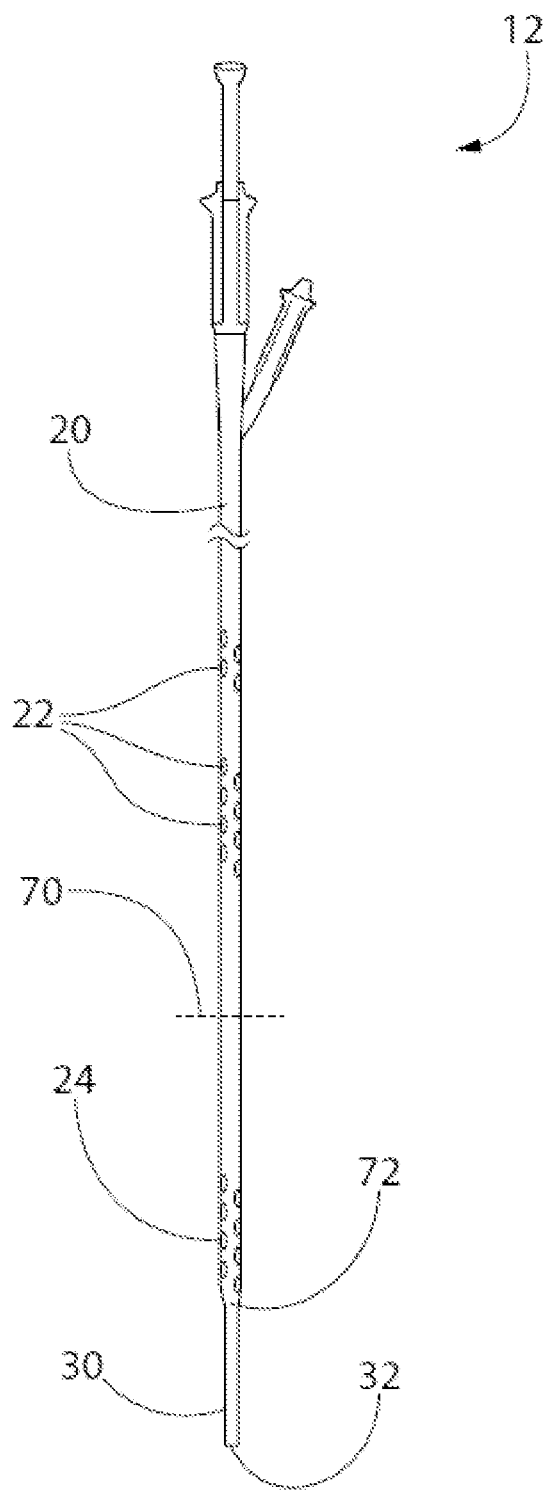
Figure 4A:
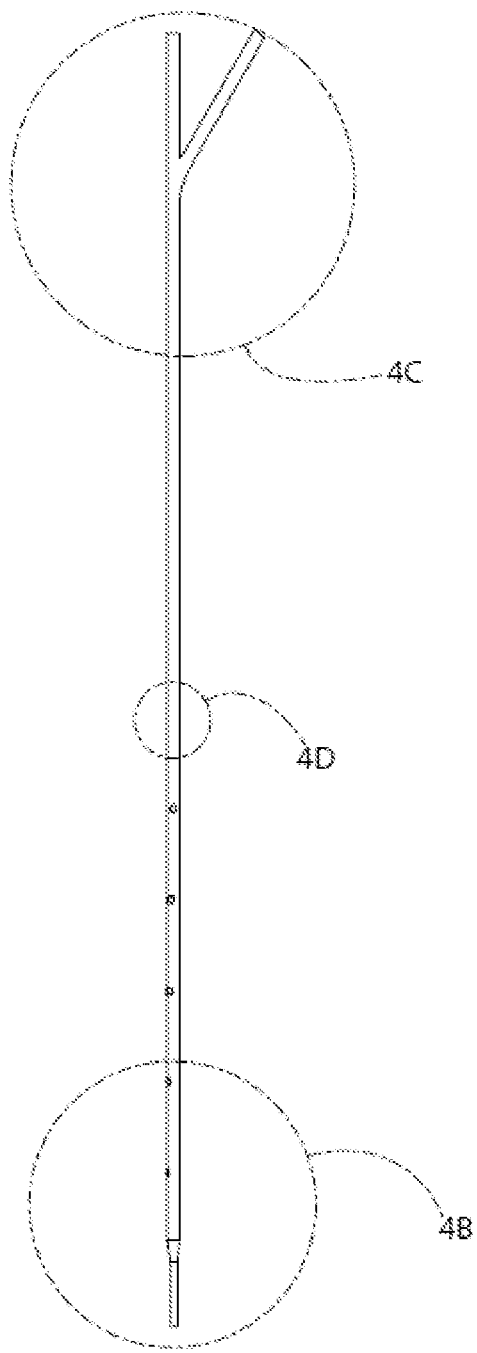
Figure 4B:
Figure 4C:
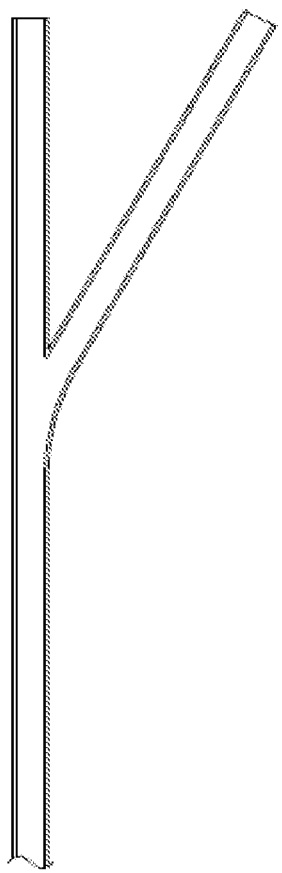
Figure 5:
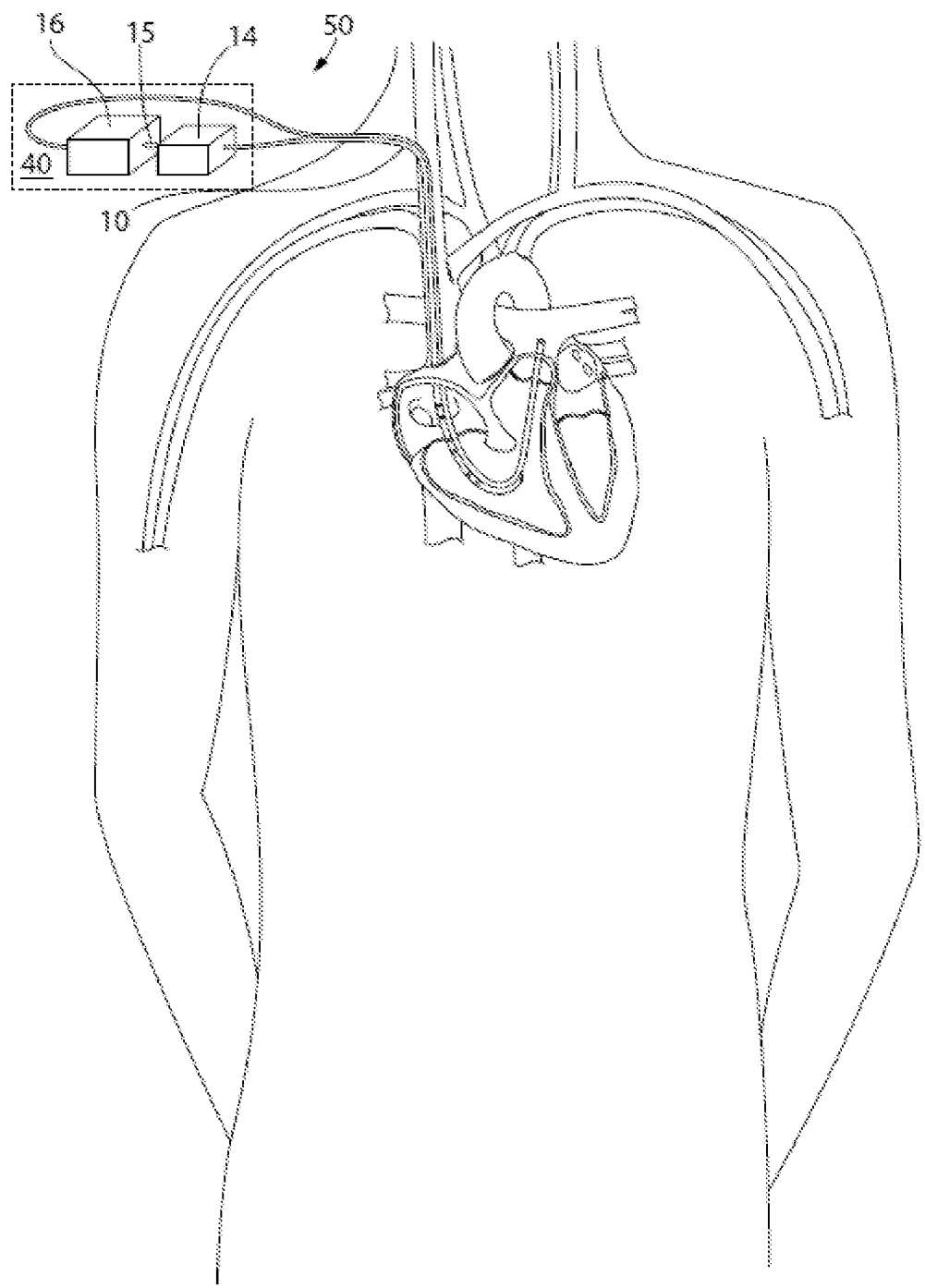
FIG. 5 is a diagram of an exemplary embodiment a catheter positioned within a subject's heart and connected to an exemplary embodiment of a portable lung assist device.
Figure 6:
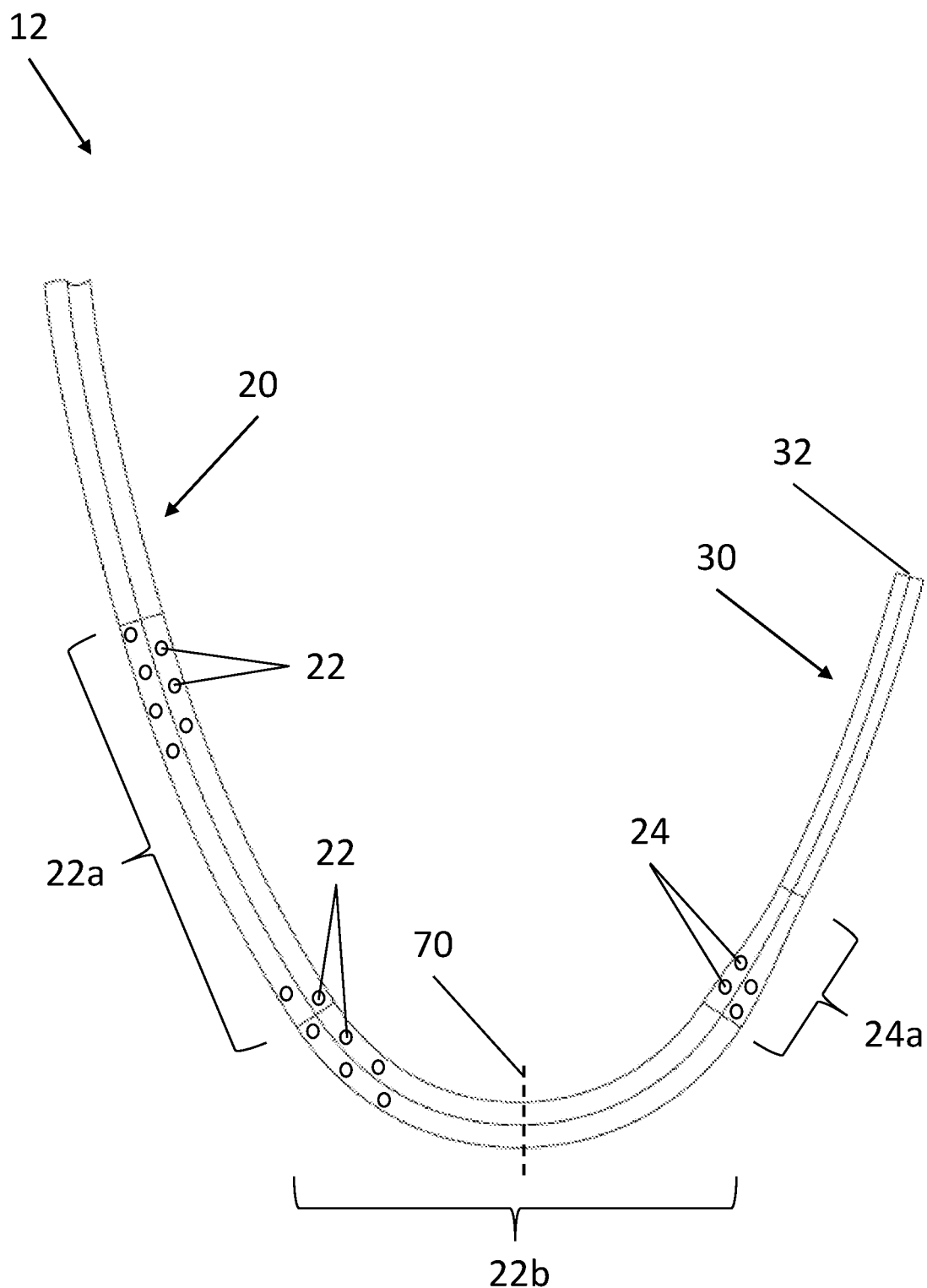
FIG. 6 is a diagram depicting a curvature in an exemplary embodiment of a coaxial catheter of the present invention.

Referring now to FIG. 3A and FIG. 3B, straight-line diagrams of a catheter 10 and a catheter 12 are depicted for the purposes of exemplary illustration. It should be appreciated that the embodiments of FIG. 3A and FIG. 3B may further include the designated curvature as shown in FIG. 4D and FIG. 6. Referring now to FIG. 3A, an embodiment of catheter 10 similar to that as shown in FIG. 2 is depicted in a straight-line diagram. Catheter 10 may generally include parallel tubes 20 and 30. Tube 20 includes openings 22 and 24 suitable for being positioned within a patient's superior vena cava, right atrium, and right ventricle for draining blood from the patient. In certain embodiments, opening 24 and optionally a portion of openings 22 are positioned within the right ventricle to drain blood directly from the right ventricle. Tube 30 includes an opening 32 suitable for returning blood to the patient after oxygenation. Tube 30 is generally longer than tube 20 so that a portion of the distal end can be positioned within the pulmonary artery.

In another embodiment and as shown in FIG. 3B, catheter 12 may include tubes 20 and 30 that can be configured coaxially. In such an embodiment, tube 30 is the inner tube of the coaxial arrangement, wherein tube 30 extends beyond a point 72 where outer tube 20 fuses with at least a portion of the wall of tube 30. The proximal end of catheter 12 comprises a branched connector having at least two connections, one for each tube. In some embodiments, a preformed curvature in catheter 12 comprises a vertex or inflection point located approximately at point 70 (see FIG. 6), such that openings 22 are positioned within the patient's superior vena cava and/or right atrium, while at least one of openings 24 are positioned within the patient's right ventricle to drain blood directly from the right ventricle. Opening 32 at or near the distal end of catheter 12 can then be positioned within the patient's pulmonary artery.

It should also be appreciated that the catheters of the present invention are not limited to any particular dimensions of length, gauge or other sizing characteristic. Accordingly, the catheters of the present invention can be any size, depending on the size or dimensions of the patient's body. For example, in certain embodiments a coaxial catheter can have a tube 20 with typical lengths between 300 and 500 mm measured from the branched connector and a tube 30 with typical lengths between 350 and 600 mm. In other embodiments, the dimensions of the catheter can be defined by lengths of drainage regions, such as a region of tube 20 having a length between 150 and 250 mm that comprises a plurality of openings 22. In other embodiments, the dimensions of the catheter can be further defined by the distance between the position of the most distal opening 22 and the position of opening 32, which can be between 50 and 150 mm. As would be understood by a person skilled in the art, the length of the catheters and the location of the various openings must be designed such that un-oxygenated blood can be suitably drained via the superior vena cava, right atrium, and/or right ventricle, while oxygenated blood can be returned at least to the patient's pulmonary artery. For example, another embodiment of a coaxial catheter of the present invention is shown in FIG. 4A through FIG. 4E, including specific dimensions and location of openings. In certain embodiments, the diameter of the lumens in the catheter of the present invention will be sized to allow flow of about 3 to 4 L per minute of blood. Similarly, the size and location of the openings in the catheter tubes may be sized to maintain such a flow rate. In one embodiment, the openings may be sized as large as possible without compromising the integrity of the catheter. However, the catheter can be sized to allow for more or less blood flow than 3 to 4 L per minute depending on a number of factors, including, but not limited to, the efficiency of the connected lung assist device or the need of blood oxygenation assistance of the patient. For example, in some embodiments, the catheter can be sized to allow for blood flow rates of 5, 6, 7, or 8 L per minute or more, or 0.5, 1, 1.5, or 2 L per minute or less.

As described elsewhere herein, the catheter of the present invention may comprise one or more curved regions for a better fit within the anatomy of the heart and for better placement of the openings within their respective regions. The curved regions are preferably preformed, such as by heat setting. In some embodiments, the curved regions are at least partially flexible, such that the curved regions may be temporarily straightened using a stylet, or such that the curved regions may be advanced over a guidewire. The curve represents an unexpected finding that by having a set curve within the parameters set forth herein, the catheters of the present invention significantly reduce damage to the heart upon insertion and placement, and create an improved draining and return flow of blood through the respective lumens due to the fact that the catheters are able to sit within the heart in a relaxed state without exerting unnecessary pressure upon tissue or requiring a rigid guidewire or stylet to remain in place. This pre-set curvature is specifically designed to allow stable positioning of the catheter against the right ventricular septum. FIG. 2, FIG. 4D, FIG. 5, and FIG. 6 depict several embodiments of exemplary catheters comprising a curve in the distal region of tubes 20 and 30 to angle the catheter into the right ventricle and pulmonary artery.

Referring now to FIG. 6, the curvature is depicted in detail. FIG. 6 is an exemplary embodiment of a catheter having first tube 20 and second tube 30 in a coaxial design (similar to FIG. 3B) and depicts the arc of the curvature relative to the positions of the various openings of the catheters of the present invention, wherein the positions of the various openings are depicted as covering a length of the catheter. For example, a curvature of the catheter begins in a first length having openings 22 within region 22a, peaks at a vertex or inflection point near point 70 in a second length having openings 22 within region 22b, continues through a third length having openings 24 within region 24a, and ends at the distal tip of the catheter with opening 32. In some embodiments, first tube 20 terminates in a distal end that is fused to second tube 30 at the vertex or inflection point of the curvature, thereby allowing stable positioning of the catheter against the right ventricular septum. The curvature can begin at the proximal end of region 22a between 270 and 310 mm from opening 32, with the vertex or inflection point of the curvature at point 70 positioned 130 to 170 mm from opening 32. A typical curvature of region 22b can be between 110° and 120°. It should be understood that the angles and lengths of the curvature are not limited to the disclosures herein can have any suitable range dependent on the size or dimensions of the patient's body and heart. When positioned in a patient's heart, the curvature allows the catheter to position openings 22 in the superior vena cava and the right atrium. Additional openings 22 can be positioned past the tricuspid valve in the right ventricle along with openings 24. Near openings 24, the catheter makes almost a U-turn to direct opening 32 through the pulmonary valve and into the pulmonary artery trunk.

The catheter of the present invention may be constructed from any materials currently known in the art used in the construction of catheters, and particularly catheters associated with lung assist devices for insertion into a patient's vasculature. In one embodiment, at least a portion of one or both tubes of the dual lumen catheter of the present invention are reinforced with wire. The wire reinforcement can be designed accordingly so that catheter can be suitably advanced into position within the patient, and so that the catheter is stabilized in the optimal location, once positioned. Accordingly, the catheter of the present invention may include portions or regions having the desired stiffness, rigidity or flexibility necessary for proper insertion into the subject and subsequent functionality. Accordingly, catheter 10 can be positioned within the patient so that the inflow openings 22 and 24 in first tube 20 can be positioned at several sites within the patient, such as the right ventricle, the right atrium, and superior vena cava, while the one or more outflow openings 32 located at the distal tip of second tube 30 can be positioned to deliver the oxygenated blood into the main pulmonary artery. The multitude of inflow openings 22 and 24 significantly improve the flow dynamics of the blood that is being drained from the patient. Further, the distance between the inflow and outflow openings 22 and 24 provides the significant and unexpected result of minimal or no re-circulation of oxygenated blood. The positioning of catheter 10 in the patient, such that the patient's pulmonary valve is between the inflow and outflow openings, also aids in preventing the re-circulation of oxygenated blood.

In addition, the configuration of the catheters of the present invention permit the catheters to be held in a more stable position than other catheters known in the art. The increased stability is due at least in part to both first tube 20 and second tube 30 being inserted through the tricuspid valve and into the right ventricle. The second tube 30 of catheter 10 is longer than first tube 20, and this longer portion of second tube 30 can be guided through the pulmonary valve and into the main pulmonary artery via methods commonly used in the art, for example a guide wire, via X-ray guidance, or ultrasound guidance. In one embodiment, the distal tip of the catheter comprises an inflatable balloon for insertion without a guide wire. Similar to a Swan-Ganz catheter, the balloon may be inflated after a portion of the catheter is inserted, whereupon the flow of blood pushes the balloon and the catheter through the blood vessels and the chambers of the heart into the desired position. The extended portion of second tube 30 also provides increased stability to the catheter by using the pulmonary valve as an additional stabilization point. In one embodiment, at least a portion of first tube 20 is fused or connected to second tube 30. In one embodiment, the entire length of first tube 20 that is to be positioned within the patient is connected to second tube 30, which provides stability to the positioning of both tubes.

Although the positioning of a portion of the catheter within the pulmonary artery is the primary reason for the high stability of the catheter within the patient, there are additional features which provide optimal stability of the catheter of the present invention. In one aspect, migration of the inserted catheter is reduced due to the use of draining points within the right ventricle. By draining the right ventricle and therefore decreasing the right ventricle blood volume, the right ventricle systolic force is reduced, thereby minimizing catheter migration. In another aspect, the degree of wire reinforcement of first tube 20 and second tube 30 can be modified to provide optimal flexibility and to minimize the chances of kinking. In another aspect, the transition zone between first tube 20 and second tube 30 is strategically designed to be positioned within the right ventricle when catheter 10 is properly inserted and stabilizes catheter 10 against the interventricular septum of the patient's heart.

In another embodiment, the catheters of the present invention may further include a means for measuring pressure. The pressure measuring means may be provided by any suitable mechanism, such as by a fluid-filled lumen. Typical fluid-filled lumen pressure measuring systems comprise a lumen having one end open to the fluid to be measured and the other end connected to a sensing diaphragm and a pressure transducer. As fluid pressure changes, the sensing diaphragm is deformed. The pressure transducer converts these mechanical changes into electrical signals, which are interpreted by a processor to calculate fluid pressure.

Figure 7:
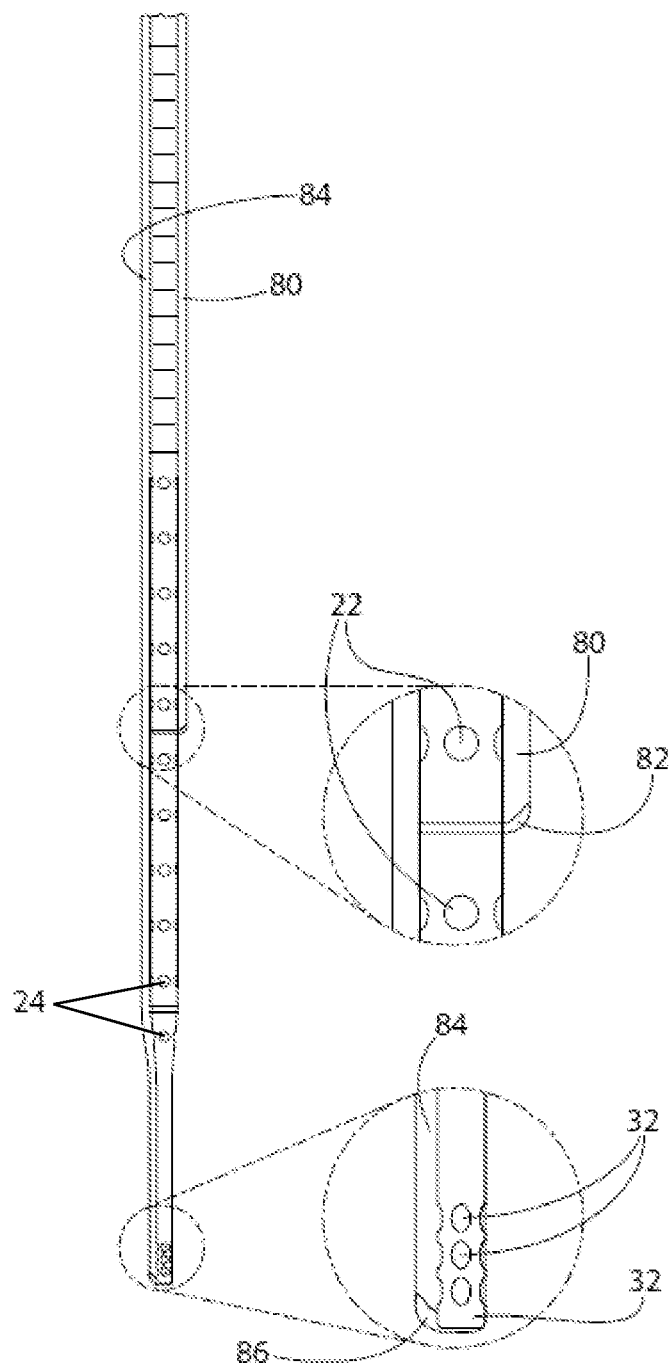
FIG. 7 is an illustration showing an exemplary embodiment of the device of the present invention further comprising at least one measuring lumen.

As shown in FIG. 7, in some embodiments, the pressure measuring means may be provided by lumen 80. Lumen 80 comprises a length, a width, a proximal end, and a distal end. The length can be any suitable length, such as a length that is at least as long as a catheter of the present invention. The width can be any suitable width, such as between 0.5 mm and 2 mm. The distal end comprises opening 82 that is in fluid communication with blood. Opening 82 permits blood to fill lumen 80, wherein blood is in contact with the proximal end comprising a pressure measuring means, such as a sensing diaphragm and pressure transducer (not pictured). Persons skilled in the art will understand that the pressure measuring means may comprise additional features common to the art, such as one or more stopcocks located along the length of the at least one lumen 80 to flush out blood and prevent clotting.

In some embodiments, lumen 80 may be positioned on the exterior of the catheters of the present invention. In other embodiments, lumen 80 may be built such that it is at least partially internal to the catheters of the present invention. An internally built lumen may comprise a portion that is external to the catheter, such as a distal portion to provide an opening 82 that is external to the catheter.

The placement of opening 82 provides a targeted pressure measurement. For example, opening 82 may be placed within a patient's superior vena cava to obtain a blood pressure measurement from within the superior vena cava.

In some embodiments, an exemplary catheter of the present invention may comprise additional lumens. For example, in one embodiment, the catheter comprises a first lumen 80 having a first opening 82 and a second lumen 84 having a second opening 86. The first opening 82 may be positioned adjacent to openings 22, wherein the first opening 82 may measure blood pressure in the superior vena cava, the right atrium, or the right ventricle. The second opening 86 may be positioned adjacent to opening 32, wherein the second opening 86 may measure blood pressure in the pulmonary artery.

The placement of opening 82 and opening 86 provide a means of monitoring pressure for diagnosis and treatment purposes. For example, in one embodiment, detecting pressures in the range of 30 to 100 mmHg in the pulmonary artery can indicate pulmonary hypertension. In another embodiment, detecting initial pressures in the range of 0 to 100 mmHg in the right ventricle of a patient having right ventricular failure, followed by subsequent measurements of pressures below 30 mmHg in the right ventricle can indicate effective right ventricular decompression using the catheters of the present invention.

Figure 8:
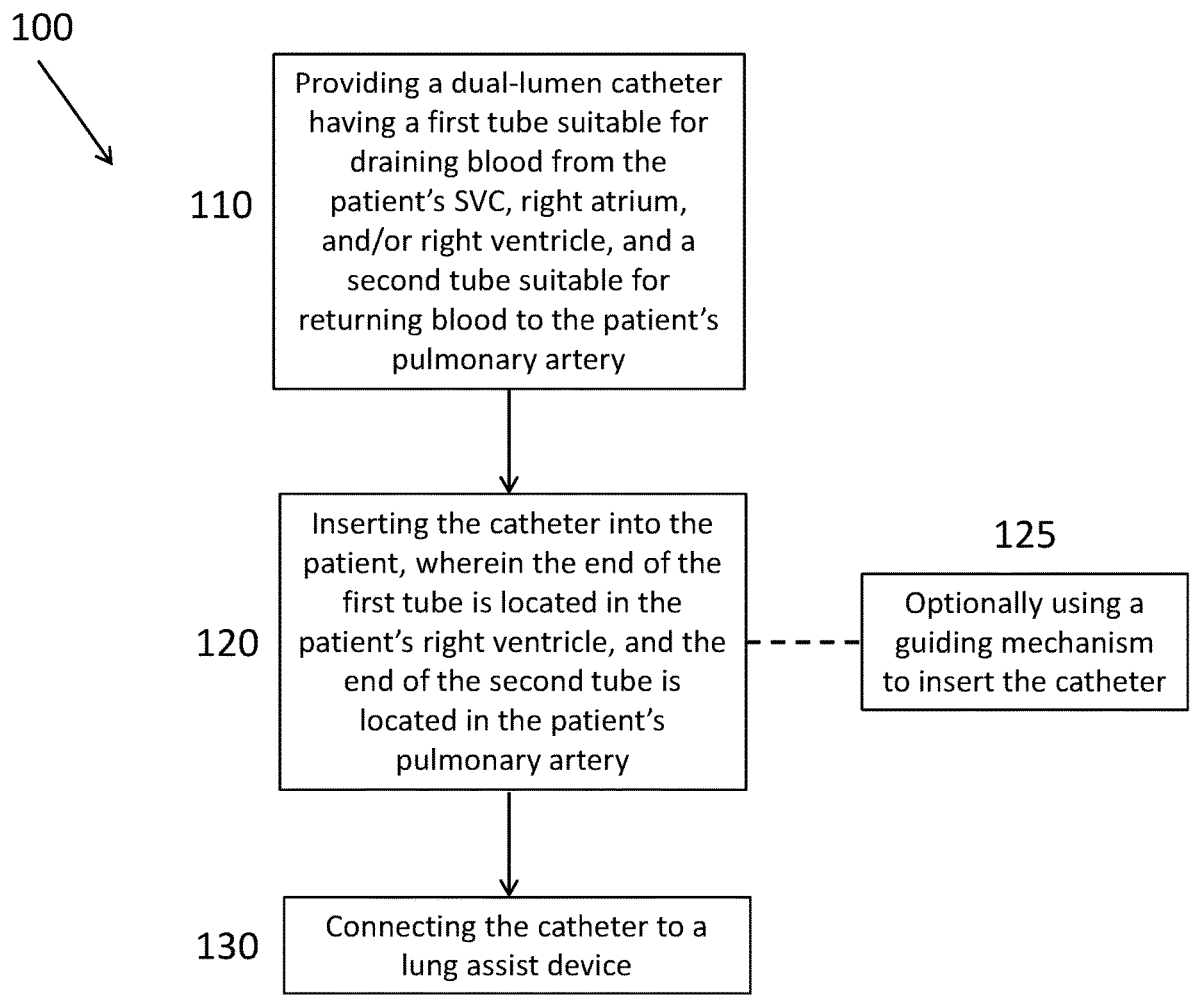
FIG. 8 is a flow diagram of one embodiment of the method of the present invention.

The present invention also relates to methods for oxygenating blood in a subject. As contemplated herein, the methods generally include the steps of inserting a catheter comprising a first tube and a second tube into a subject, such that the catheter enters the subject's heart via superior vena cava, passes through the right atrium and right ventricle, and extends into the pulmonary artery, draining blood from the subject's right ventricle via the first tube, oxygenating the drained blood, and returning the oxygenated blood to the subject's pulmonary artery via the second tube. For example, referring to FIG. 8, in one embodiment, the method 100 of the present invention comprises the steps of: (110) providing a dual-lumen catheter comprising two tubes, wherein the first tube comprises a lumen suitable for draining blood from the SVC, right atrium, and/or right ventricle of a patient, and the second tube comprises a lumen suitable for returning oxygenated blood from a lung assist device to the pulmonary artery of the patient; (120) inserting the catheter into the patient such that the end of the first tube is located in the patient's right ventricle, and a portion of the first tube having openings for draining blood is located in the SVC, right atrium, and/or right ventricle, and such that the second tube, which is connected to the first tube, is fed through the tricuspid valve, through the right ventricle, through the pulmonary valve, and into the pulmonary artery, wherein the portion of the second tube having openings, i.e., the end of the second tube, is located in the pulmonary artery; and (130) connecting the catheter to a lung assist device such that un-oxygenated blood is removed from the patient's SVC, right atrium, and/or right ventricle via the first tube, and oxygenated blood is returned to the patient's pulmonary artery via the second tube. In one embodiment, the method comprises the step of inserting the catheter using a guidance mechanism, for example, but not limited to, a guide wire or X-ray guidance system (125). In one embodiment, the patient's blood is oxygenated via an ECMO or other lung assist device. In another embodiment, the system mechanically supports a failing right ventricle using an external pump.

The disclosures of each and every patent, patent application, and publication cited herein are hereby each incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A cannula configured for use with a lung assist device, comprising:
   a first tube with at least one first opening, at least one second opening, and a section without openings between the first and second openings, wherein the at least one first opening is configured to drain un-oxygenated blood from a right ventricle of the subject's heart, the at least one second opening is configured to drain un-oxygenated blood from a right atrium of the subject's heart, and the section without openings is configured to align with a tricuspid valve of the subject's heart when the first and second openings are situated in the right ventricle and right atrium, respectively, wherein the first tube is fluidly connected to the lung assist device such that the drained un-oxygenated blood from the first and second openings is transferred to the lung assist device;
   a second tube, coaxial with the first tube and fluidly connected to the lung assist device, the second tube having at least one second opening configured to return oxygenated blood from the lung assist device to a pulmonary trunk of the subject.

2. A cannula configured for use with a lung assist device, comprising:
   a first tube having a first section with a first set of multiple openings along a first length, a second section with second set of multiple openings along a second length, and a third section without openings between the first and second set of multiple openings, wherein the first set of multiple openings is configured to drain un-oxygenated blood from a right ventricle of a subject's heart, the second set of multiple openings is configured to drain un-oxygenated blood from a right atrium of the subject's heart, and the third section without openings is configured to align with a tricuspid valve of the subject's heart when the first and second set of multiple openings are situated in the right ventricle and right atrium, respectively, wherein the first tube is fluidly connected to the lung assist device such that the drained un-oxygenated blood from the first and second openings is transferred to the lung assist device; and
   a second tube fluidly connected to the lung assist device, the second tube having at least one second opening configured to return oxygenated blood from the lung assist device to a pulmonary trunk of the subject.

* * * * *